United States Patent
Minato

[11] Patent Number: 6,039,447
[45] Date of Patent: Mar. 21, 2000

[54] ARTIFICIAL VISION SYSTEM

[75] Inventor: Atsuo Minato, Tokyo, Japan

[73] Assignee: Hoya Corporation, Japan

[21] Appl. No.: 09/257,202

[22] Filed: Feb. 25, 1999

[30] Foreign Application Priority Data

Mar. 6, 1998 [JP] Japan .................................. 10-055384

[51] Int. Cl.[7] .................................................. A61B 3/10
[52] U.S. Cl. ................................................................ 351/216
[58] Field of Search ..................................... 351/205, 216, 351/217, 218, 219, 221, 246, 247, 176, 237; 250/227.2; 382/258, 266; 623/4

[56] References Cited

U.S. PATENT DOCUMENTS

| | | | |
|---|---|---|---|
| 4,628,210 | 12/1986 | Hobrough | 250/558 |
| 5,033,103 | 7/1991 | Sillart | 382/266 |
| 5,532,770 | 7/1996 | Schneider et al. | 351/205 |
| 5,546,142 | 8/1996 | Kobayashi | 351/237 |
| 5,726,443 | 3/1998 | Immega et al. | 250/227.2 |

FOREIGN PATENT DOCUMENTS

| | | |
|---|---|---|
| 0 734 683 A2 | 10/1996 | European Pat. Off. . |
| 0 810 427 A1 | 12/1997 | European Pat. Off. . |

*Primary Examiner*—George Manuel
*Attorney, Agent, or Firm*—Griffin, Butler, Whisenhunt & Szipl, LLP

[57] ABSTRACT

An artificial vision system which simulates a retinal image obtained when a subject views a standard measuring object by turning his eyeball with respect to an eyeglass lens. An artificial vision lens system corresponding to an ocular optical system and a CCD camera having a CCD plane corresponding to a retina are provided within an artificial vision camera. Rotary movement of the eyeball centering on its turning point with respect to an eyeglass lens is simulated by turning the artificial vision camera in the horizontal direction by a rotary stage and by turning the glass lens in the vertical direction by another rotary stage. Turning and parallel movement mechanisms are provided under a stage on which the lens and the artificial vision camera are mounted so that the artificial vision camera always points toward a predetermined position on the standard object as viewed through the lens.

16 Claims, 12 Drawing Sheets

|  | RADIUS OF CURVATURE (mm) | GAP BETWEEN FACES (mm) | REFRACTIVE INDEX | ABBE'S NUMBER |
|---|---|---|---|---|
| L1 | r1 = -7.05 | | n1 = 1.80610 | ν1 = 33.3 |
| | r2 = -13.41 | r1~r2 = 1.00 | | |
| L2 | r3 = -8.43 | r2~r3 = 2.40 | n2 = 1.51680 | ν2 = 64.4 |
| STOP | r4 = ∞ | r3~r4 = 1.50 | | |
| L3 | r5 = 39.73 | r4~r5 = 1.95 | n3 = 1.56384 | ν3 = 60.8 |
| | r6 = -23.46 | r5~r6 = 2.14 | | |
| L4 | r7 = 11.53 | r6~r7 = 0.20 | n4 = 1.58913 | ν4 = 61.2 |
| | r8 = -154.30 | r7~r8 = 4.71 | | |
| L5 | r9 = 9.56 | r8~r9 = 0.20 | n5 = 1.71300 | ν5 = 54.1 |
| | r10 = 34.68 | r9~r10 = 2.00 | | |
| L6 | r11 = -108.00 | r10~r11 = 0.20 | n6 = 1.80610 | ν6 = 33.3 |
| | r12 = 5.71 | r11~r12 = 1.00 | | |

FIG. 8

| OPTICAL SYSTEM / OPTICAL CONSTANTS | ARTIFICAL VISION LENS | | GLUSTRAND'S SIMULATED EYE (D-LINE) |
|---|---|---|---|
| | E-LINE | D-LINE | |
| FOCAL LENGTH | 17.039mm | 17.052mm | 17.053mm |
| REFRACTING POWER | 58.69D | 58.64D | 58.64D |
| BACK FOCUS | 10.98mm | 10.99mm | |
| F NUMBER | 2.54 | 2.54 | |
| OBJECT SIDE PRINCIPAL POINT | 1.325mm | 1.350mm | 1.348mm |
| IMAGE SIDE PRINCIPAL POINT | −7.057mm | −7.060mm | |
| POSITION OF PUPIL ENTRANCE | 2.753mm | 2.759mm | 3.047mm |
| POSITION OF PUPIL EXIT | −5.739mm | −5.759mm | |

FIG.9

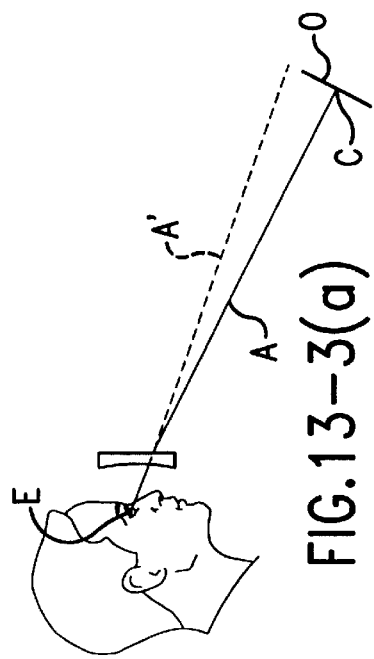
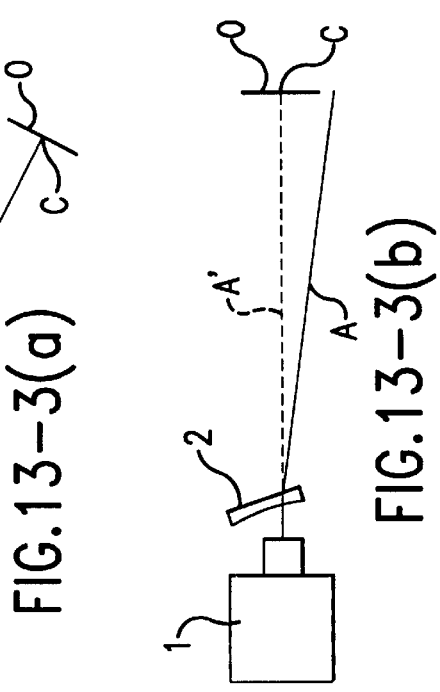
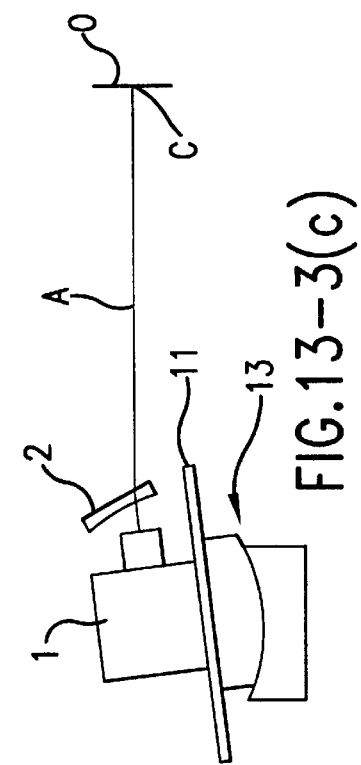
FIG.13-3(a)　　　FIG.13-3(b)　　　FIG.13-3(c)
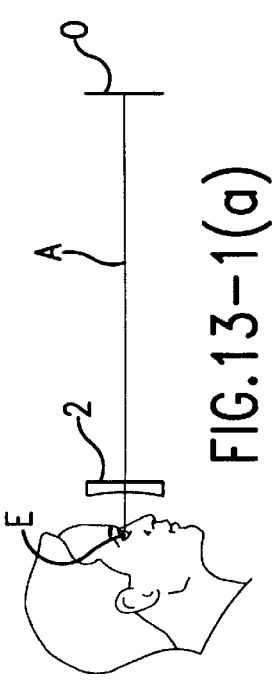
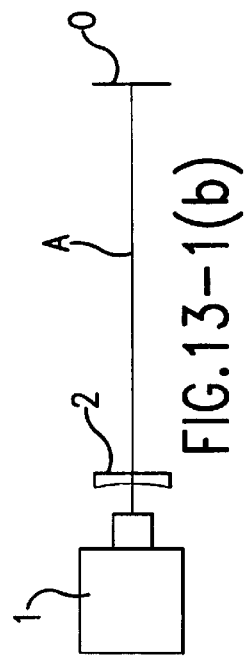
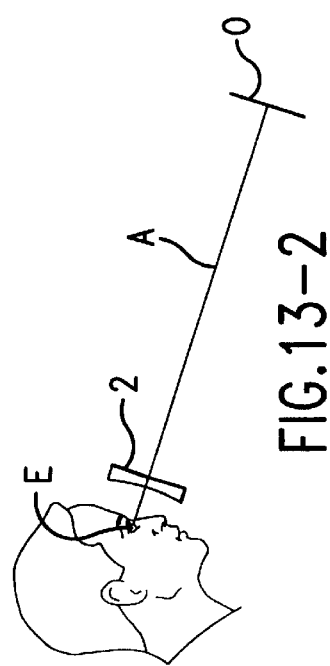
FIG.13-1(a)　　　FIG.13-1(b)　　　FIG.13-2

ARTIFICIAL VISION SYSTEM

FIELD OF THE INVENTION

The present invention relates to an artificial vision system which allows simulation in real time of sight of objects seen by an observer wearing eyeglasses, and more particularly to an artificial vision system which simulates a retinal image when an observer views an object through different regions of an eyeglass lens by changing the direction of a line of sight. The invention further relates to a method of simulating a retinal image obtained when an observer views an object through a lens by turning his eyeball.

BACKGROUND AND RELATED ART

Because an ocular optical system is very complicated and an actual eye is very difficult to handle, various eye simulations have been proposed as a standard optical model of an eyeball. Studies on the optical characteristics of an eyeball (e.g., changes of various optical images when an intraocular lens is implanted) have been conducted by using such simulated eyes or by computer simulation using optical constants calculated from such simulated eyes.

Various new types of lenses such as a progressive multi-focus lens are being developed in the field of eyeglass lenses. However, it has heretofore been a problem that it has not been possible to objectively observe how things are seen when a subject wears these eyeglass lenses. This problem has been a big obstacle in the research and development of eyeglass lenses.

The inventors of the present invention have devised an ocular optical simulation system (Japanese Patent Publication No. Hei. 301887) for simulating a retinal image obtained when a subject wears an eyeglass lens. This system has an eye simulating lens and comprises a lens system for simulating an optical system of human eyes when a subject wears an eyeglass lens utilizing the eye simulating lens, an eyeglass lens to be simulated and an image-pickup means for picking up an image formed by the lens system, in order to simulate a retinal image of a subject wearing the eyeglass lens.

It is necessary to consider differences between ordinary optical systems (camera, telescope and the like) in simulating the optics of an eyeglass lens and an eyeball. That is, although an object in a wide range can be imaged on the face of a film at one time in case of the ordinary optical system, e.g., a camera, as shown in FIG. 14a, the eyeball receives an image in a wide range while turning centering about a turning point as shown in FIG. 14b. This is because not all images imaged on the retina of the eye are perceived as clear images and only an image in a narrow area of the fovea part having high resolution is seen as a clear image. Accordingly, it is necessary to take the rotary movement (ocular movement) centering on the turning point of the eyeball into consideration in simulating the eyeglass lens and the eyeball as one optical system.

Furthermore, a solid (three-dimensional) standard measuring object (e.g., chart) suited for the purpose of using the eyeglass lens (e.g., far-sighted use, near-sighted use and the like) is required for the above-mentioned reason to evaluate the performance of the eyeglass lens. However, it is very difficult to dispose the measuring object (chart) widely in three-dimensional space because, for example, an appropriate installation space must be assured.

Accordingly, it is an object of the present invention to provide an artificial vision system which can simulate a retinal image at each eye position when a subject observes a standard object by turning his eyeball with respect to the eyeglass lens.

Another object of the present invention is to provide an artificial vision system which can simulate the positional relationship among the eyeglass lens, the eyeball and the standard object at each eye position when a subject views the standard object through the eyeglass lens by turning his eyeball to the standard object set at a predetermined position, and which can simulate a retinal image at each position of the eyeball.

SUMMARY OF THE INVENTION

In order to achieve the above-mentioned objects, the present invention provides an artificial vision system for simulating a retinal image at each position when a subject puts on an eyeglass lens and views a standard measuring object by turning the eyeball. The system comprises an artificial vision camera having an artificial vision lens system corresponding to an ocular optical system and a planar image-pickup corresponding to a retina. A rotating mechanism is provided for turning the artificial vision camera relatively with respect to the eyeglass lens around a turning point of the artificial vision lens system in order to simulate ocular movement by which the eyeball turns centering on its turning point with respect to the eyeglass lens.

Because the artificial vision camera is turned relatively with respect to the eyeglass lens around a turning point of the artificial vision lens system, the positional relationship between the eyeglass lens and the eyeball when the eyeball is turned may be simulated. Accordingly, the system according to the invention allows the observation of changes in the retinal image when a subject observes a standard measuring object through different positions of the eyeglass lens by changing the direction of the line of sight.

The turning of the artificial vision lens system around the turning point may be realized by turning the artificial vision camera relatively with respect to the eyeglass lens around two axes (e.g., one axis in the vertical and one in the horizontal direction) passing through the turning point of the artificial vision lens system and orthogonal to each other. In this case, the artificial vision camera corresponding to the eyeball may be turned around the vertical and horizontal axes with respect to the eyeglass lens by fixing the eyeglass lens like the actual relationship between the eyeglass lens and the eyeball or one of the artificial vision camera and the eyeglass lens may be turned around the vertical axis and the other around the horizontal axis.

A second embodiment of the artificial vision system for simulating a retinal image at each position when a subject puts on an eyeglass lens and views a standard measuring object by turning his eyeball comprises: an artificial vision camera having an artificial vision lens system corresponding to an ocular optical system and a planar image-pickup corresponding to a retina; and mechanisms for applying parallel movement and rotation to the eyeglass lens and the artificial vision camera so that the artificial vision camera points toward the direction of the standard measuring object at a predetermined position through the eyeglass lens while simulating the positional relationship between the eyeglass lens and the eyeball in each position.

According to the second embodiment of the invention, the parallel movement and turning are applied to the eyeglass lens and the artificial vision camera to simulate the positional relationship between the eyeglass lens and the eyeball when the eyeball is turned similar to the first embodiment so that the artificial vision camera always points toward the standard measuring object at a predetermined position through the eyeglass lens.

Because a eyeglass lens refracts light like a prism, the visual axis (optical axis) passing through the eyeglass lens is refracted by the eyeglass lens. Therefore, the positional relationship among the eyeball, the eyeglass lens and the standard measuring object cannot be precisely simulated just by relatively turning the eyeglass lens and the artificial vision camera. Therefore, according to a second embodiment of the invention, parallel movement and turning are applied to the eyeglass lens and the artificial vision camera so that the visual axis (optical axis) of the artificial vision camera faces in front of the measuring object and so that the visual axis (optical axis) of the artificial vision camera coincides with the center of the measuring object at each measuring position when a subject views the standard measuring object through the eyeglass lens by turning his eyeball.

Accordingly, the retinal image obtained when one watches the measuring object through different regions of an eyeglass lens by turning one's eyeball may be simulated by laying out the artificial vision camera, the standard measuring object, etc., one-dimensionally according to the invention, so that the simulation may be carried out in a small space with simple facilities.

A third embodiment of the artificial vision system for simulating a retinal image at each turn position when a subject puts on an eyeglass lens and views a standard measuring object by turning his eyeball, comprises: an artificial vision camera having an artificial vision lens system corresponding to an ocular optical system and a planar image-pickup corresponding to a retina; a rotating mechanism for turning the artificial vision camera relatively with respect to the eyeglass lens around a turning point of the artificial vision lens system in order to simulate an ocular movement by which the eyeball turns centering on its turning point with respect to the eyeglass lens; and mechanisms for applying three-dimensional turning to stages on which the eyeglass lens, the artificial vision camera and the rotating mechanism are placed so that the artificial vision camera points toward the direction of the standard measuring object set at a predetermined position through the eyeglass lens.

According to the invention, the visual axis (optical axis) of the artificial vision camera may be made to always face in front of the standard measuring object by providing a mechanism for applying three-dimensional turning to the stages on which the eyeglass lens, the artificial vision camera and the above-mentioned turn mechanism are mounted.

A fourth embodiment of the artificial vision system for simulating a retinal image at each turn position when one puts on an eyeglass lens and watches a standard measuring object by turning his eyeball, comprises: an artificial vision camera having an artificial vision lens system corresponding to an ocular optical system and a planar image-pickup corresponding to a retina; a rotating mechanism for turning the artificial vision camera relatively with respect to the eyeglass lens around a turning point of the artificial vision lens system in order to simulate an ocular movement by which the eyeball turns centered on its turning point with respect to the eyeglass lens; and mechanisms for applying three-dimensional turning and parallel movement to stages on which the eyeglass lens, the artificial vision camera and the rotating mechanism are placed so that the artificial vision camera points toward the direction of the standard measuring object at predetermined position through the eyeglass lens.

This fourth embodiment realizes the same motion as the second embodiment with respect to the eyeglass lens and the artificial vision camera. To that end, the three-dimensional parallel movement and turning are applied to the stages. In this manner, the visual axis (optical axis) of the artificial vision camera faces in front of the standard measuring object. Thus, the visual axis (optical axis) of the artificial vision camera coincides with the center of the measuring object at each measuring position when an observer views the standard measuring object through the eyeglass lens by turning his eyeball. At the same time, the positional relationship between the eyeglass lens and the eyeball at each turn position is kept the same, while simulating the ocular movement with respect to the eyeglass lens by relatively turning the artificial vision camera with respect to the eyeglass lens by using the rotating mechanism on the stage similarly to the first embodiment.

In the first through fourth embodiments described above, preferably, the artificial vision lens system is designed based on optical constants of a paraxial area calculated from the simulated eye so as to be able to simulate the positional relationship between an eyeglass lens and an object side principal point of an eyeball.

The use of this artificial vision lens system allows the eyeglass lens to be disposed at a desired position on the object side from the front face of the artificial vision lens system (corresponds to the front face of the cornea), the turning point to be disposed at a desired position on the image side from the front face of the artificial vision lens system, and the positioning of the eyeglass lens and the eyeball to be simulated correctly. While only a narrow retinal image at the fovea part is clearly perceived by human eyes, the image in this narrow field of view may be simulated fully by designing the artificial vision lens system based on a simulated eye (such as Glustrand's precision simulated eye) whose optical constants (focal length, position of pupil entrance, etc.) in the paraxial area are not so different from those of the human eye. In addition, the artificial vision lens system may be relatively easily manufactured.

Preferably, the optical system of the artificial vision lens system comprises, sequentially from the object side, a front lens group having negative refracting power, a stop, and rear lens group having positive refracting power, and the optical system is arranged such that the focal position can be controlled by moving the rear lens group. By constructing the system as described above, the focal position may be controlled without changing the position of the pupil entrance of the artificial vision lens system.

Characteristics equivalent to human vision, etc. others may be realized, and the artificial vision camera may be constructed compactly by using CCDs as the planar image-pickup in the above-mentioned embodiments. Still more, the retinal image obtained when one puts on the eyeglass lens may be observed in real-time by providing display means for displaying the image picked up by the artificial vision camera.

In accordance with a still further embodiment of the present invention, there is provided an artificial vision system for simulating a retinal image obtained when an observer views an object through a lens by turning his eyeball. The system comprises: an artificial vision camera including an artificial ocular optical system having a simulated turning point and a planar image-pickup; a lens holder; and a mechanism operably connected to the artificial vision camera to rotate the artificial vision camera around the simulated turning point relative to a lens held in the lens holder. In accordance with yet another embodiment according to the present invention, there is provided a system otherwise as in the latter embodiment having a first mechanism operably connected to the artificial vision camera to rotate the artificial vision camera around the simulated turning point relative to a lens held in the lens holder; and a second mechanism operably connected to the holder, to position a lens held in the lens holder relative to the artificial vision camera.

In accordance with a still further embodiment, the system is provided with a first mechanism operably connected to the artificial vision camera to rotate the artificial vision camera around the simulated turning point relative to a lens held in the lens holder; a second a mechanism operably connected to the lens holder to position a lens held in the holder relative to the artificial vision camera; and a standard object; wherein the first and second mechanisms are operably connected to position said artificial vision camera to point through a eyeglass lens held in the lens holder toward a predetermined location on said standard object.

In yet another embodiment, the system is provided with a first mechanism operably connected to the artificial vision camera to rotate the artificial vision camera around the simulated turning point relative to a lens held in the lens holder; a second mechanism operably connected to the lens holder to position a lens held in the holder relative to the artificial vision camera; a third mechanism operably connected to the first mechanism and second mechanisms to impart rotation and parallel movement to the lens holder and artificial vision camera; and a standard object; wherein the first and second mechanisms are operably connected to position the artificial vision camera to point through a eyeglass lens held in the lens holder toward a predetermined location on said standard object.

A still further embodiment of the present invention provides a method of simulating a retinal image obtained when an observer views an object through a lens by turning his eyeball. The method comprises the steps of: providing an artificial vision camera including an artificial ocular optical system having a simulated turning point and a planar image-pickup; providing a lens holder for holding a lens; providing a lens; and moving the lens and the artificial vision camera to simulate movement of the artificial vision camera about the turning point.

Further objects, features and advantages of the present invention will become apparent from the Detailed Description of the Preferred Embodiments, which follows, when considered together with the attached Figures.

BRIEF DESCRIPTION OF DRAWINGS

FIG. 8 is a table showing illustrative numerical data such as radius of curvature of each lens face of the artificial vision lens system according to the present invention.

FIG. 9 is a table showing illustrative optical constants such as a focal length of the artificial vision lens system according to the present invention.

FIGS. 13-1(a) through 13-3(c) are diagrams for explaining rotary and parallel movements of the artificial vision camera and the eyeglass lens to simulate the positional relationship between an eyeball, the eyeglass lens and the measuring object when the eyeball is turned.

DETAILED DESCRIPTION OF THE PREFERRED EMBODIMENTS

Figure 1:
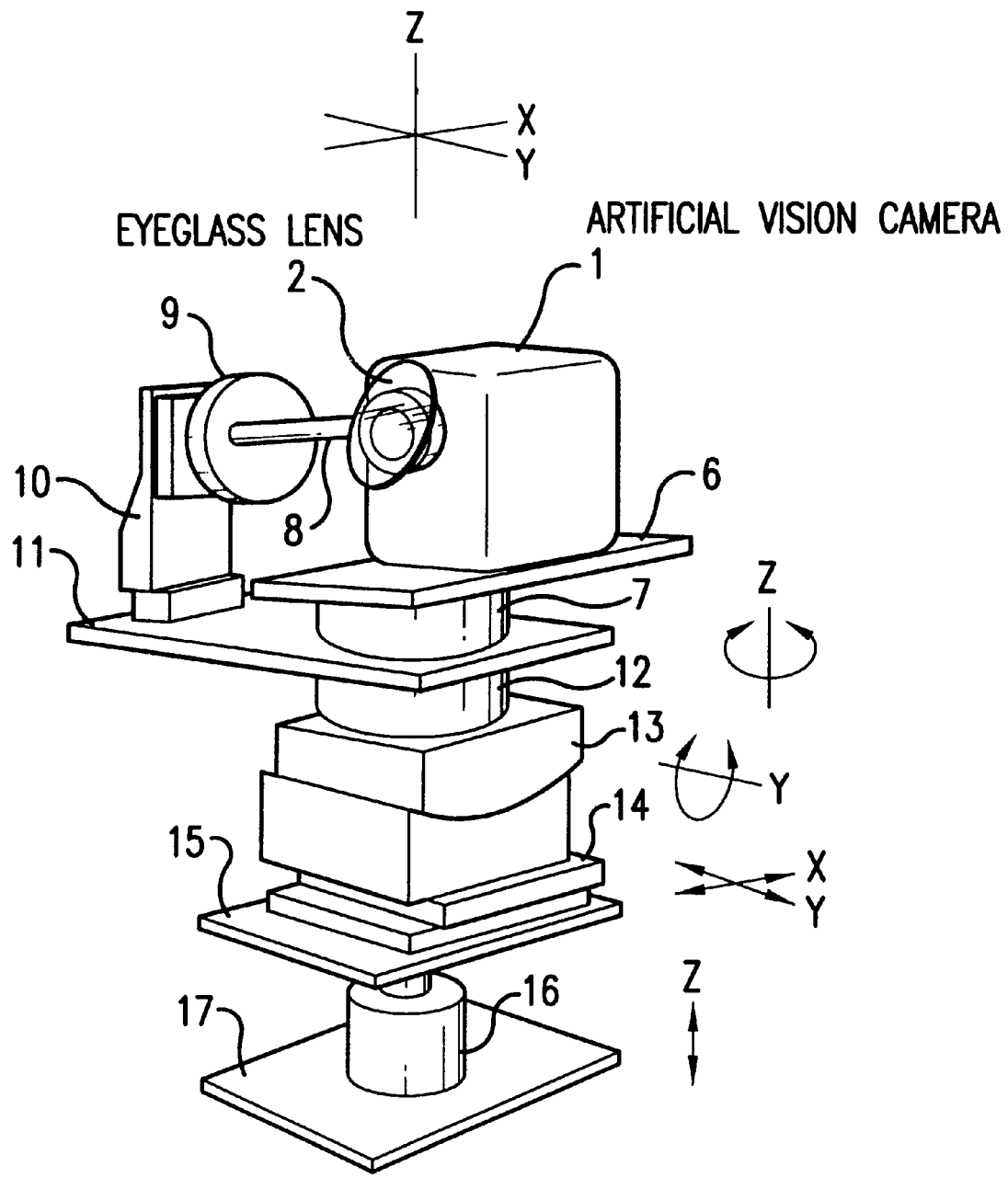
FIG. 1 is a perspective view showing one embodiment of an artificial vision system of the present invention.

The invention will now be described with reference to certain preferred embodiments, and with reference to the Figures in which like parts are referred to by like reference numerals.

Figure 2A:
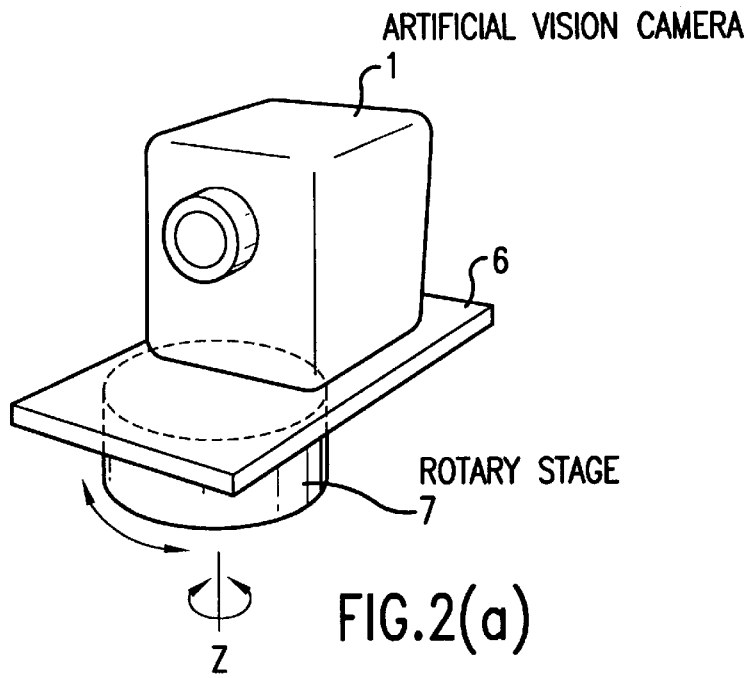
FIGS. 2a through 2c are explanatory diagrams for explaining the rotation of the artificial vision camera and eyeglass lens shown in FIG. 1.
Figure 2B:
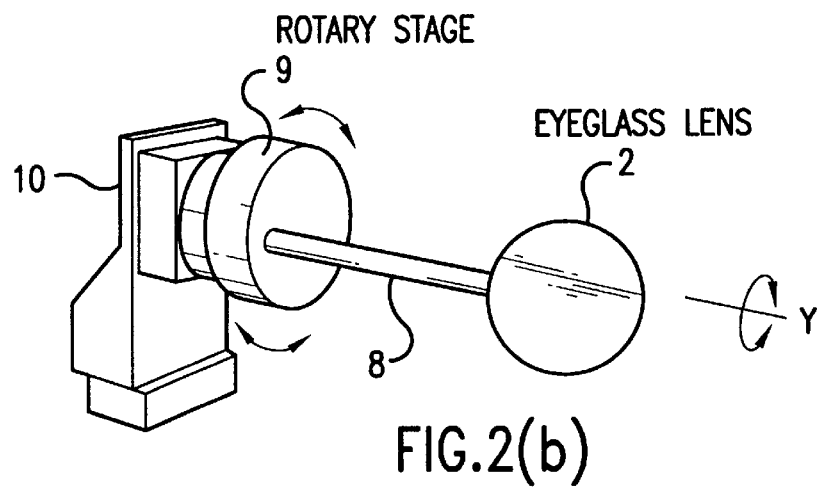

FIG. 1 is a perspective view of one embodiment of an artificial vision system according to the present invention. In FIG. 1, the reference numeral (1) denotes an artificial vision camera 1. An artificial vision lens system corresponding to an ocular optical system and a CCD camera having CCDs which function as an planar image-pickup corresponding to a retina are provided within artificial vision camera 1. Eyeglass lens 2 is provided in front of the artificial vision camera 1 so as to face an artificial vision lens system 3 as shown in FIGS. 1 through 3. A system structure is required which allows (1) an optical axis (or a visual line) and an image surface to be continuously evaluated, and (2) the position of the eyeglass lens where light flux passes through to be changed in accordance to the rotation of the eyeball. This structure simulates the effect of the rotary movement of the eyeball centering on its turning point with respect to the eyeglass lens.

Figure 2C:
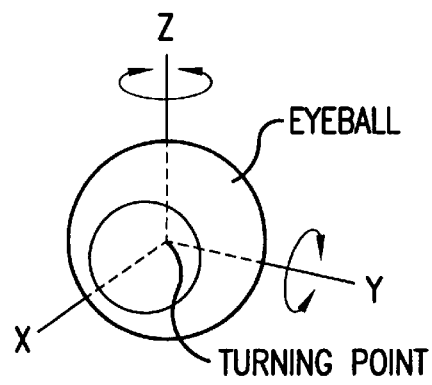
Figure 3:
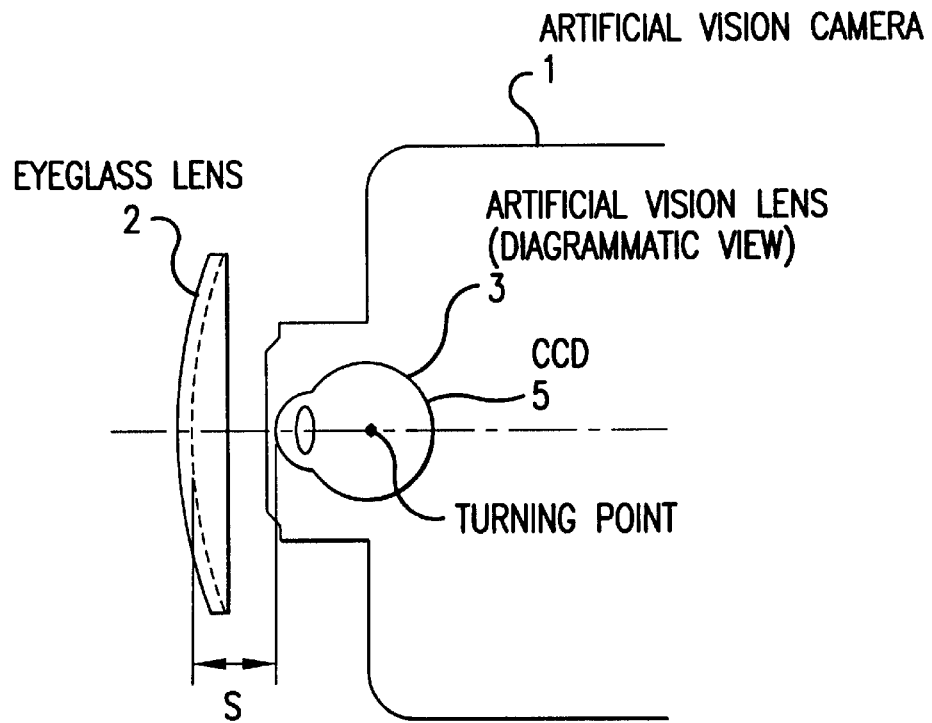
FIG. 3 is a diagram showing the positional relationship between the eyeglass lens and an artificial vision lens system within the artificial vision camera.

The rotary movement (ocular movement) of the eyeball around the turn point may be realized by combining rotation in the horizontal direction (rotation around a Z-axis passing through the turning point of the eyeball) and rotation in the vertical direction (rotation around a Y-axis passing through the turning point of the eyeball) as shown in FIG. 2c. According to the present embodiment, the rotary movement of the eyeball is simulated such that rotation in the horizontal direction (rotation around a Z-axis passing through a turning point of the artificial vision lens system) is carried out by the artificial vision camera 1 and rotation in the vertical direction (rotation around a Y-axis passing through the turning point of the artificial vision lens system) is carried out by the eyeglass lens 2.

That is, rotation in the horizontal direction (right and left direction in FIG. 1) is made possible by placing the artificial vision camera (artificial vision lens system and CCD camera) 1 on a mount 6 on a rotary stage 7 as shown in FIGS. 1 and 2a. Furthermore, the artificial vision camera 1 is arranged such that its position can be adjusted with the center of rotation of the rotary stage 7 so that the position of the center of rotation of the rotary stage 7 coincides with the position of the turning point of the artificial vision lens system. This configuration achieves the same effect as rotary movement of the eyeball in the horizontal direction around the turning point.

The eyeglass lens 2 is attached to a rotary stage 9 via a supporting rod 8 as shown in FIGS. 1 and 2b so that the eyeglass lens 2 can be turned in the vertical direction (up and down direction in FIG. 1) by turning the rotary stage 9. The system is arranged such that a distance S from the rear face of the eyeglass lens 2 to the first face (corresponding to the apex of a cornea of an eyeball) of the artificial vision lens system 3 may be adjusted as shown in FIG. 3, so that the position of the center of rotation of the rotary stage 9 coincides with the position of the turning point of the artificial vision lens system 3. In this manner the same effect as the rotary movement of an eyeball in the vertical direction centering on the turning point may be obtained.

Figure 4:
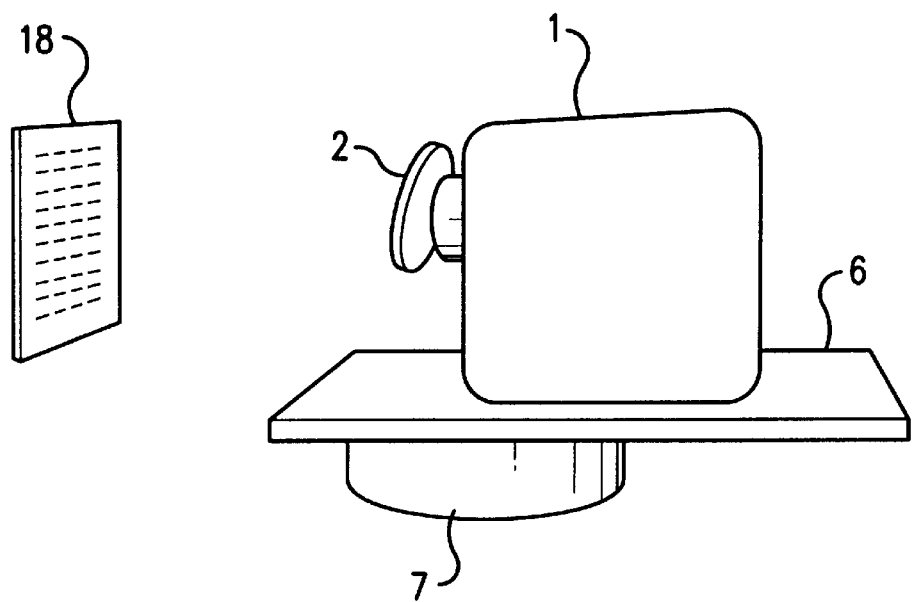
FIG. 4 is a perspective view showing a state in which the artificial vision camera is viewing a standard measuring object through a near-sighted section of the eyeglass lens.

The same effect as the rotary movement (ocular movement) of an eyeball centering on its turning point may be obtained by appropriately combining these two rotary movements in the horizontal and vertical directions. FIG. 4 shows one example of observing a standard measuring object by using the artificial vision camera 1 in which the artificial vision camera 1 views a nearby standard measuring object 18, such as a newspaper, or optical chart, through a near-sighted section of the eyeglass lens (e.g., multi-focus lens) 2.

Rotary stage 7 for turning the artificial vision camera 1 and a supporting section 10 for supporting rotary stage 9 for turning the eyeglass lens 2 are provided on a stage 11. The eyeglass lens 2 and the artificial vision camera 1 are arranged so as to be able to turn by about 30 degrees, respectively, in the up and down and right and left directions.

It is necessary, in evaluating the performance of the eyeglass lens (by the standard object or chart), to observe a retinal image at each position, when the position of light flux, which is transmitted from the standard object (chart) on the outside through the eyeglass lens, changes along with turning of the eyeball. It is very difficult to realize this objective, because a large number of standard objects or charts have to be set within a three-dimensional space or field of vision (in a wide area in a wide range of positions in the up and down and right and left directions and from up-close positions to distant positions) visible by changing a line of sight when the artificial vision camera corresponding to an eyeball is turned (up and down or right and left) around the turning point.

In the present embodiment, the chart (or other standard measuring object) is fixed in one direction and three-dimensional turning and parallel movement are achieved by the artificial vision camera 1 and the eyeglass lens 2 to simulate the positional relationship between the eyeball, the eyeglass lens and the chart or standard object when the eyeball turns. A turning and parallel movement mechanism is provided under the stage 11 on which the eyeglass lens 2 and the artificial vision camera 1 are mounted. The mechanism is arranged so that the optical axis (visual axis) of the artificial vision camera 1 always faces the chart (or other standard measuring object) in a predetermined direction while simulating the rotary movements of an eyeball centered on the turning point with respect to the eyeglass lens. This is achieved by turning in the horizontal direction of the artificial vision camera 1 by means of the rotary stage 7 and turning in the vertical direction of the eyeglass lens 2 by means of the rotary stage 9, as described above.

The above movements can be explained concretely by setting the direction of the optical axis (visual axis) of the artificial vision camera 1 to be the X-direction, the direction to the right and left with respect to the eyeglass lens 2 to be the Y-direction and the direction up and down with respect to the eyeglass lens 2 as Z-direction as shown in FIG. 1. Mounted right under the stage 11 on which the eyeglass lens 2 and the artificial vision camera 1 are mounted is a rotary stage 12 turning around the Z-axis, a gonio-stage 13 turning around the Y-axis, an XY stage 14 moving in parallel to the X and Y directions and an a Z stage 16, at the bottom of the FIG. moving in parallel to the Z-direction. The assembly is also arranged such that the rotation about the X-axis is achieved by processing an image taken into the artificial vision camera 1 (it is noted that the reference numeral (15) denotes a mount plate of the XY stage 14 and (17) denotes a base board).

Thereby, the optical axis (visual axis) of the artificial vision camera 1 may be set so as to always point toward the chart (or standard measuring object) at a fixed direction through the eyeglass lens 2. That is, the positional relationship between the eyeball, the eyeglass lens and the measuring object when the eyeball is turned may be simulated even with the standard measuring object at a fixed position by applying three-dimensional rotary and linear movements to the artificial vision camera 1 and the eyeglass lens 2. This relationship will be explained more concretely below.

FIG. 13-1(a) shows a case in which a subject wearing an eyeglass lens 2, such as a progressive multi-focus lens, is viewing a standard measuring object O through a far-sighted section of the eyeglass lens 2, while keeping his posture straight and line of sight horizontal. In this state, a visual axis (optical axis) A of an eyeball E is a straight line which passes through the eyeglass lens 2. The relationship among the eyeball E, the eyeglass lens 2 and the measuring object O at this time may be simulated by keeping a visual axis (optical axis) A of the artificial vision camera 1 horizontal as shown in FIG. 13-1(b) because the visual axis (optical axis) A advances linearly through the far-sighted section and faces the front of the measuring object O. FIG. 13-2 shows a case in which the subject tilts his neck (head) down without moving the eyeball E from the state shown in FIG. 13-1(a), the relationship among the eyeball E, the eyeglass lens 2 and the measuring object O is the same as that shown in FIG. 13-1(a) and may also be simulated as shown in FIG. 13-1(b).

However, when the subject views the standard measuring object O below him through the near-sighted section of the eyeglass lens 2 by moving only the eyeball E as shown in FIG. 13-3(a), the visual axis (optical axis) A of the eyeball E does not coincide with a straight line A' which advances linearly and extends through the eyeglass lens 2 as shown in FIG. 13-1(a). It is because the eyeglass lens 2 functions as a prism and the visual axis (optical axis) A is deflected by the eyeglass lens 2 and the eyeball E looking not in the A' direction but in the A direction.

Accordingly, when only the eyeglass lens 2 is turned upward around the turning point of the artificial vision lens system as shown in FIG. 13-3(b), in order to simulate the downward turn of the eyeball E without changing the positional relationship between the artificial vision camera 1 and the measuring object O (while keeping the same state with that shown in FIG. 13-1(b), the visual axis (shooting direction of the artificial vision camera 1) A of the artificial vision camera 1 does not advance linearly through the eyeglass lens 2 like a straight line A', but is deflected by the eyeglass lens 2 and does not face the front of the measuring object O (fixed). The performance of the eyeglass lens 2 cannot be evaluated correctly in such a case.

Therefore, the gonio-stage 13 under the stage 11 is turned while keeping the positional relationship (state in FIG. 13-3(b)) between the artificial vision camera 1 and the eyeglass lens 2 on the stage 11 as shown in FIG. 13(3)c so that the visual axis (optical axis) A of the artificial vision camera 1 points to the front of the measuring object O (fixed). Furthermore, the artificial vision camera 1 and the eyeglass lens 2 are moved up and down by the Z stage 16 under the stage 11 to adjust the assembly so that the visual axis (optical axis) A of the artificial vision camera 1 is positioned at the center point C of the measuring object O at each measuring position to simulate the case when the measuring object O is seen through the eyeglass lens 2 by turning the eyeball E.

The method for correcting the deflection of the visual axis (optical axis) A of the artificial vision camera 1 has been described, for simplicity's sake and referring respect to FIG. 13, only with respect to deflection in the vertical direction caused by the eyeglass lens 2 when the eyeball E is turned. However, the visual axis (optical axis) A of the artificial vision camera 1 may actually be deflected through the eyeglass lens 2, not only in the vertical direction, but also in the horizontal direction when the eyeball E is turned in the vertical and horizontal directions.

Accordingly, the positional relationship between the eyeball E (and the eyeglass lens 2) and the measuring object O is simulated by a three-dimensional turning and parallel movement mechanism (including the case of image processing) such as the rotary stage 12, the gonio-stage 13, the XY stage 14 and the Z stage 16 provided under the stage 11; while the vertical turning of the eyeball E itself is simulated by the vertical turning of the eyeglass lens 2 and the horizontal turning of the eyeball E itself is simulated by the horizontal turning of the artificial vision camera 1 in order to simulate the positional relationship among the eyeball E, the eyeglass lens 2 and the measuring object O.

The structure under the stage 11 for simulating the ocular movement by turning the artificial vision camera 1 and the eyeglass lens 2 may be realized by any suitable assembly having a parallel movement and turning mechanism in the direction of each of the X, Y and Z axes. For instance, it is possible to arrange the assembly so as to mount a gonio-stage turning the Y-axis right under the stage 11 and then a rotary stage turning around the Z-axis, a Z stage moving in parallel in the Z direction and an XY stage moving in parallel with the X and Y directions at the bottom. Turning around the X-axis may be realized by processing images which have been taken in.

The artificial vision lens system 3 used in the artificial vision camera 1 will next be explained.

Figure 5:
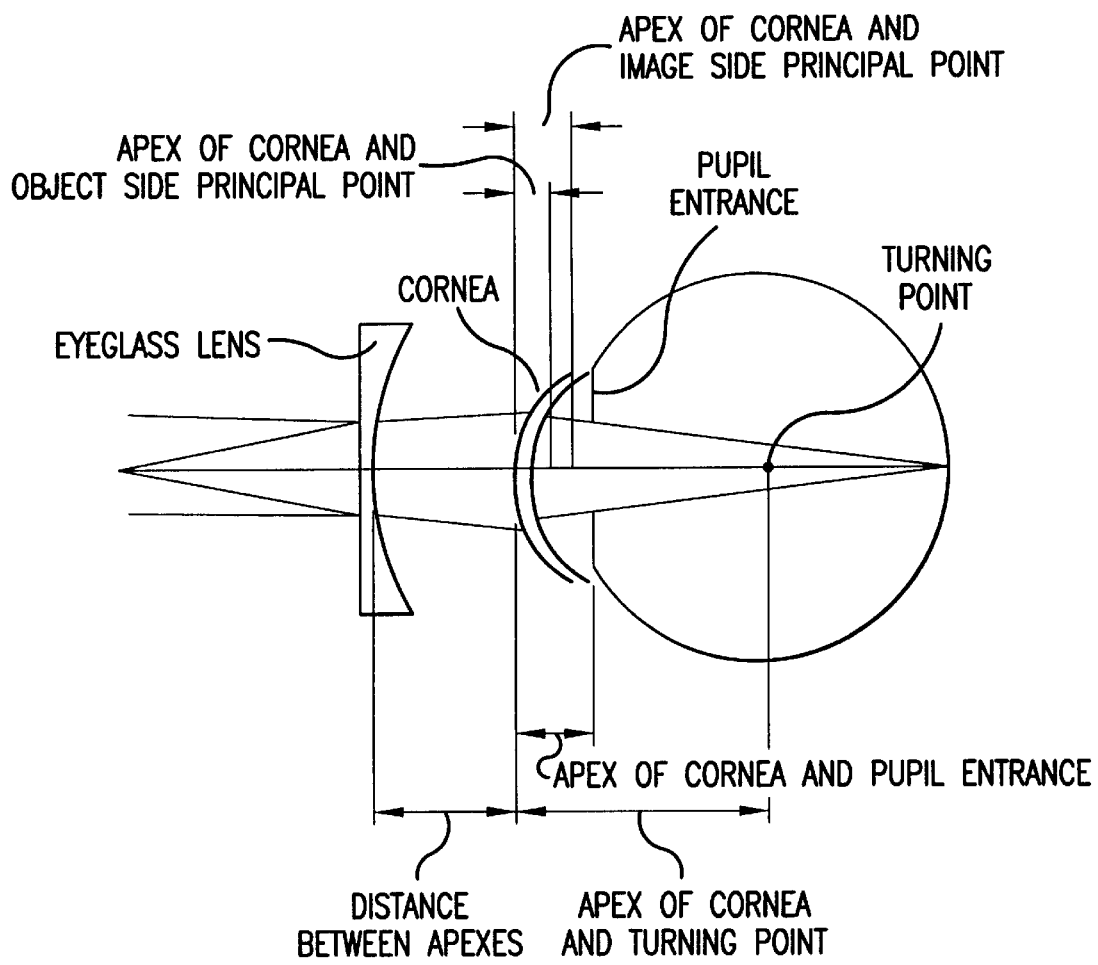
FIG. 5 is a explanatory diagram illustrating the formation of an image by the eyeglass lens and a simulated eye that replaces an eyeball.

While light which has passed through the eyeglass lens advances toward a pupil (entrance to the pupil) of the eye, the brightness of an image and the size of a view field change when a distance between the apexes of the rear face of the eyeglass lens and of the cornea and the position of the pupil (position of the entrance to the pupil) shift when the optical system replacing the eye as shown in FIG. 5 is used. Therefore, it is necessary to give due consideration to the above-mentioned distance and the position so that they can be set correctly. However, the eyeglass lens and the state of the eyeball cannot be simulated by ready-made photography and industrial lenses because the position of the object side principal point and the entrance to the pupil are located on a rear side as compared to the eyeball, and the distance between the apexes cannot be set correctly. That is, because the brightness of the image and the size of the field of view largely change in simulating the retinal image by using an eyeglass lens and an optical system such as ready made photographing lenses, the lens cannot be evaluated correctly in this fashion. Therefore, an optical system is required which allows the distance between the apexes and the position of the entrance to the pupil to be correctly set.

The artificial vision lens system 3 according to the present invention has been designed and fabricated by making reference to optical constants of a paraxial area calculated from a Glustrand's precision simulated eye so that the positional relationship between the eyeglass lens and position of the object side principal point of the eyeball may be simulated correctly.

A number of simulated eyes whose ocular image-forming characteristics are adjusted to the actual measurements have been proposed lately (e.g., one using an aspherical lens (R. Navarro, 1985), one in which a crystalline lens is multi-layered (O. Pomerantzeff, 1984) and one using a distributed index lens (J. Warren Blaker, 1980)). However, there have been technological problems in fabricating these simulated eyes. Therefore, the optical constants in the paraxial area of the Glustrand's precision simulated eye has been adopted because the optical constants (focal length, position of entrance pupil and others) of the human eye is not so different from that in the paraxial area.

Figure 6:
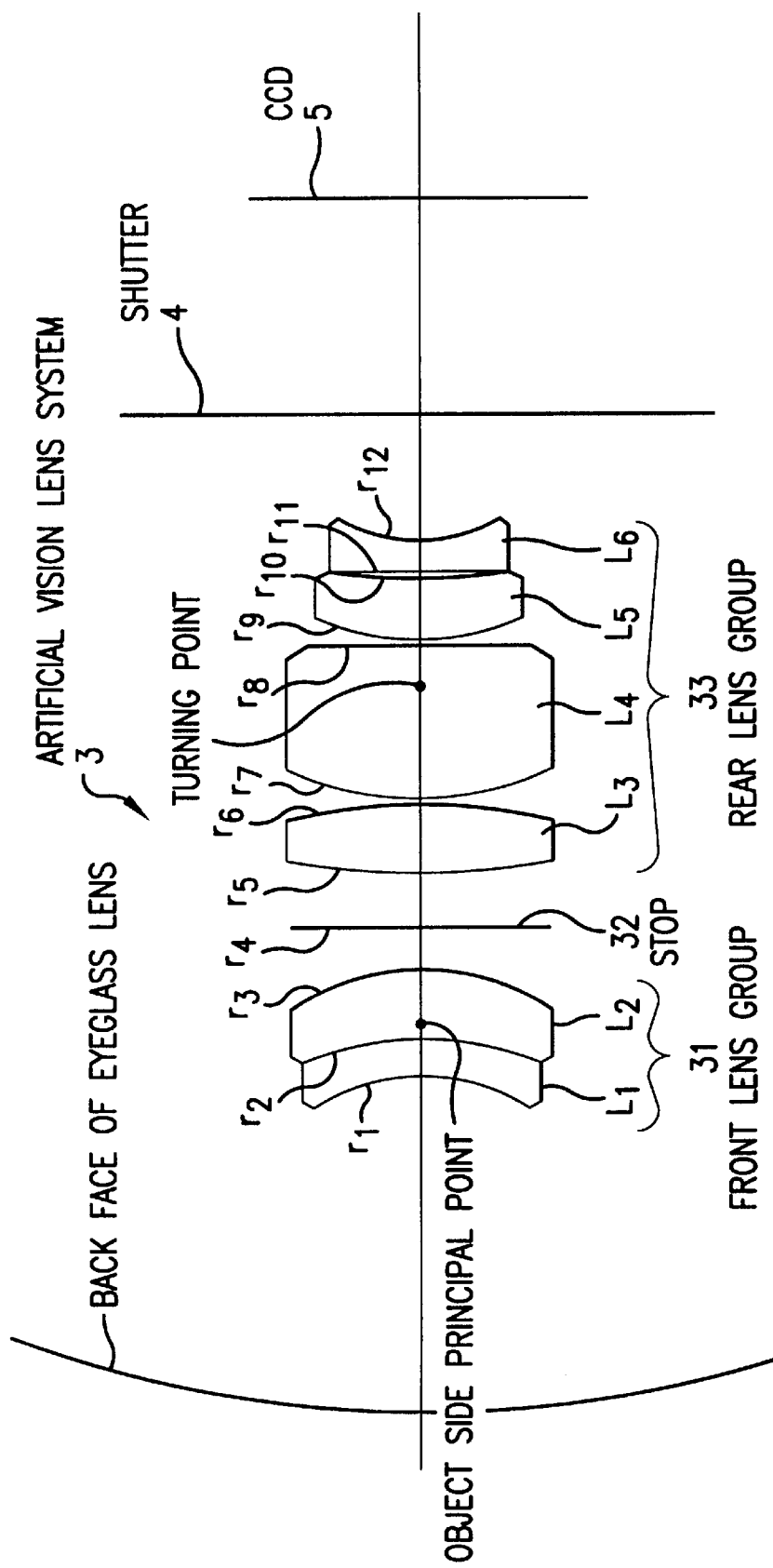
FIG. 6 is a diagram showing the disposition of the artificial vision lens system, a shutter and CCDs of a CCD camera provided within an artificial vision camera.

FIG. 6 shows the disposition of the artificial vision lens system 3, a shutter 4 of the CCD camera and the CCDs (CCD surface) 5. As shown in FIG. 6, the artificial vision lens system 3 comprises, in order from the object side, a front lens group 31 composed of lenses $L_1$ and $L_2$ and having negative refracting power, a stop 32, and a rear lens group 33 composed of lenses $L_3$ through $L_6$ and having positive refracting power. The object side principal point of the whole system and the turning point (or the pupil entrance) are disposed at positions suitable for simulating the eyeglass lens.

Figures 7A, 7B, 7C:
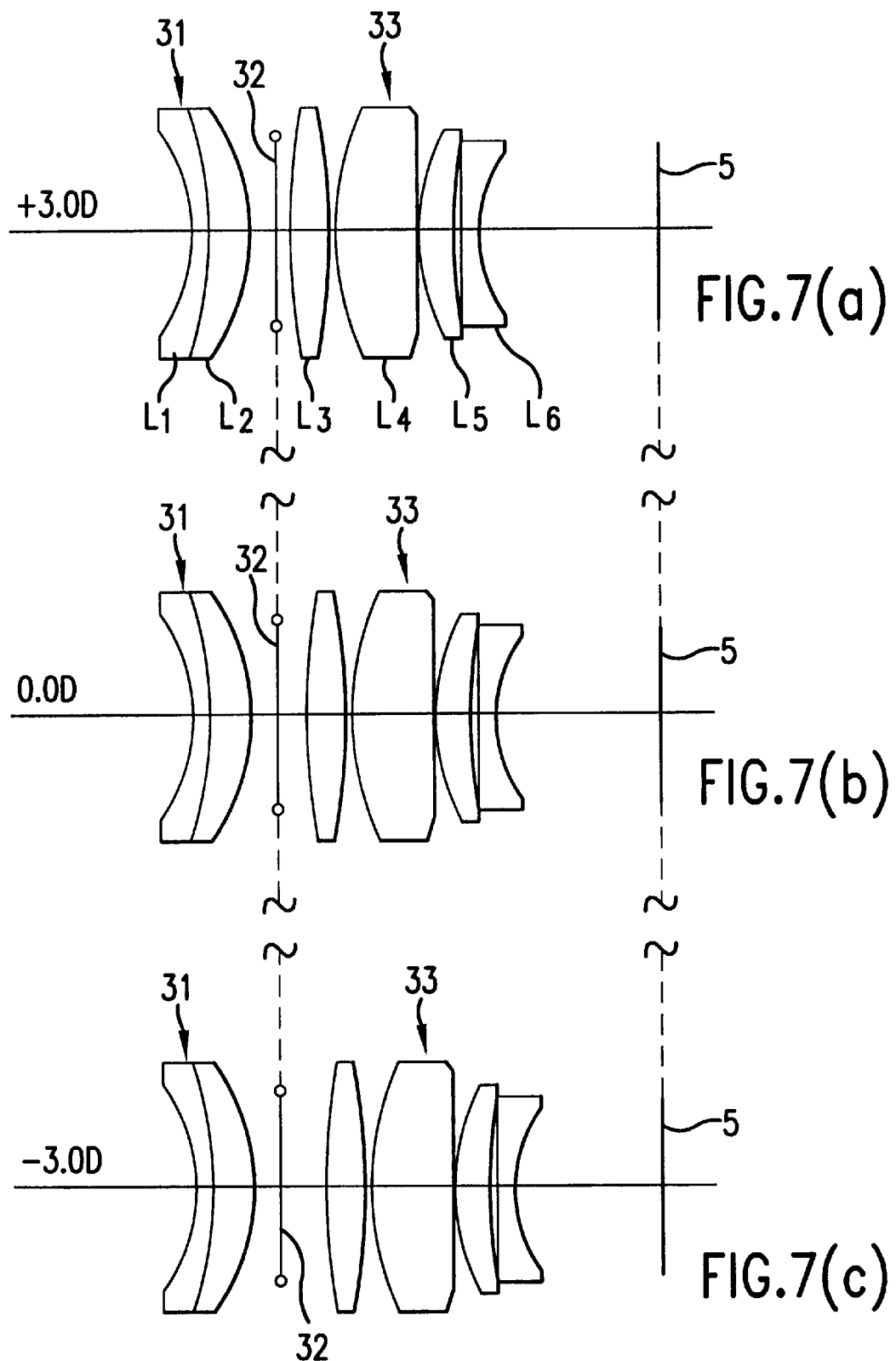
FIGS. 7a through 7c are diagrams illustrating accommodation of focal position of the artificial vision lens system.

The focal position of the artificial vision lens system 3 may be accommodated with an accommodating ability of ±3.0 D (diopter) by moving the rear lens group 33 behind the stop 32 of the optical system as shown in FIG. 7. FIG. 7b shows the reference position at 0.0 D. FIG. 7a shows a state in which the rear lens group 33 is moved forward from the state in FIG. 7b to increase the refracting power by +3.0 D, and FIG. 7c shows a state in which the rear lens group 33 is moved rearward from the state shown in FIG. 7b to reduce the refracting power by −3.0 D. Thus, the refracting power may be controlled by moving the rear lens group 33 behind the stop 32, so that the position of the pupil entrance will not change even when the focal position of the artificial vision lens system 3 is changed. Furthermore, because the refracting power of the artificial vision lens system 3 may be changed, it is possible to simulate how things can be seen corresponding to accommodating ability of eyes of respective persons having normal vision, short-sightedness, far-sightedness, old-sighted eye, and the like.

FIG. 8 shows numerical data of the lenses $L_1$ through $L_6$. In FIG. 8, the respective symbols $r_1$, $r_2$, . . . denote a radius of curvature of each lens face (including the stop) (see FIG. 6) and $r_1$ to $r_2$, $r_2$ to $r_3$, . . . denote gaps (distance on the optical axis) between the respective lens faces (including the stop) (for example, $r_1$ to $r_2$ is a distance between the front face $r_1$ and the rear face $r_2$ of the lens $L_1$ (thickness of the lens $L_1$ on the optical axis). Further, n1, n2, . . . denote refractive index of the respective lenses $L_1$, $L_2$, . . . (on a d-line) and v1, v2, . . . denote the Abbe's number of the respective lenses $L_1$, $L_2$, . . . (on the d-line). It is noted that the front face of the lens $L_2$ and the rear face r of the lens $L_1$ have the same radius of curvature $r_2$ and the lenses $L_1$ and $L_2$ are closely contacted. The gap $r_4$ to $r_5$ between the stop 32 and the front face of the lens $L_3$ changes when the rear lens group 33 is moved to change the accommodating ability of the above-mentioned artificial vision lens system 3. The value 1.95 mm of the gap $r_4$ to $r_5$ in FIG. 8 is the value in the case of FIG. 7b and the values of the gap $r_4$ to $r_5$ in case of FIGS. 7a and 7c are 0.95 mm and 2.95 mm, respectively. Furthermore, in the present embodiment, the stop 32 is a fixed stop whose diameter is $\phi 8.5$ mm. However, the diameter of the stop may be changed to $\phi 8.5$, 6.0, 4.0 or 2.0 mm.

FIG. 9 shows the optical constants of the artificial vision lens system 3 according to the above-described embodiment. Thereby, the eyeglass lens 2 may be disposed at an arbitrary position between 10 and 20 mm to the object side from the front face of the artificial vision lens system 3 and the turning point may be disposed at an arbitrary position between 10 to 22 mm to the image side from the front face of the artificial vision lens system 3.

Because the setting position may be controlled as described above, the positional relationship among the eyeglass lens and the object side principal point and the turning point of the artificial vision lens system 3 in FIG. 6 may be set in the same manner as the positional relationship between the eyeglass lens and the object side principal point and the turning point of the eyeball in FIG. 5. It is noted that the position of the pupil entrance, not the position of the turning point, may be set from the back face of the eyeglass lens or the object side principal point of the artificial vision lens system 3.

The part of the present system corresponding to the retina of a human eye is the CCD 5. Because the image surface is planar, the best image surface of the artificial vision lens system is arranged to be planar corresponding to the CCD surface. A high resolution CCD camera (Kodak Mega-plus 1.4 i) manufactured by Eastman Kodak Co. has been used as the CCD camera. An effective photo-receiving area of the CCD 5 is 100% and its pixel size is 6.8 $\mu$m×6.8 $\mu$m. This corresponds to about 150 lines/mm in terms of spatial frequency and is equivalent to a visual acuity of about 1.5.

By reducing from a visual acuity of 1.5, the MTF (Modulation Transfer Function) turns out to be 20 to 25% or more, when the spatial frequency is 150 (lines/mm) in the case of a human, It is known that the human eye presents a value more or less higher than the MTF of the Glustrand's precision simulated eye because it includes not only the optical performances of the eyeball (retina, crystalline lens and others) but also the MTF in the retina, characteristics of visual information processing mechanism in the neural network and the cerebrum, and the like (H Ohzu et, al., "Optical Modulation by the Isolated Human Fovea", Vision Res 12, 231 to 251 (1972)). From these aspects, the artificial vision lens system have been designed by setting the high-frequency side at a slightly higher value. When it is confirmed that the artificial vision lens system thus designed has been fabricated accurately, the relative evaluation and observation of the eyeglass lens may be performed favorably without being influenced very much by the fabricated artificial vision lens system.

Figure 10:
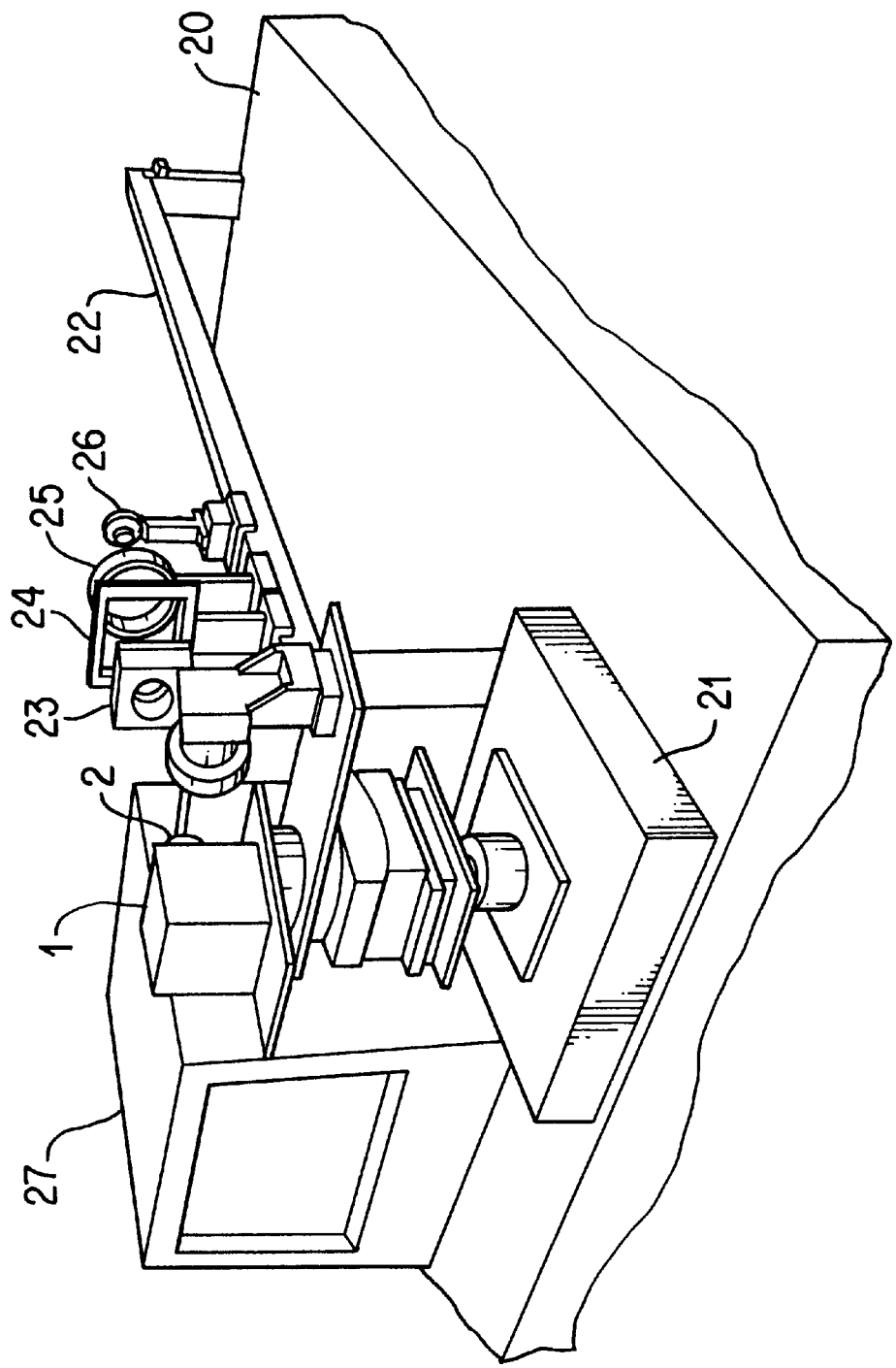
FIG. 10 is a perspective view showing a structure of a system for evaluating the performance of an eyeglass lens by observing a standard measuring object (e.g., chart) at a distance and up close by using the artificial vision system shown in FIG. 1.

While it is possible to change the distance between the standard measuring object (e.g., chart) and the eyeglass lens 2 by moving in the X-axis direction by means of the XY stage 14 described in FIG. 1, the movement is limited just by moving the XY stage 14 and the distance cannot be changed arbitrarily from a distant standard measuring object to a near one. The measuring object is fixed on the X-axis and is disposed, while changing the distance between the eyeglass lens 2 in the X-axis direction, so as to be able change the distance between the measuring object and the eyeglass lens arbitrarily. FIG. 10 shows a system for observing a standard measuring object (e.g., chart) at a distance and closely to evaluate the performance of the eyeglass lens 2 (evaluation by the chart) by using the above-mentioned artificial vision system shown in FIG. 1.

As shown in FIG. 10, the artificial vision system in FIG. 1 is set on a mount 21 on a base 20. An X rail 22 is disposed on the base 20 along the X-axis direction, which is the direction of the optical axis (visual axis) of the artificial vision camera 1. The chart, an illuminating optical system for illuminating the chart, etc. are set on the X rail 22. Specifically, disposed on the X rail 22 are a collimator box 23 on which the chart is attached, a diffusing plate 24, a collimator lens 25, an illuminator 26 and the like. A monitor 27 for displaying an image of the chart shot by the artificial vision camera 1 is provided on the base 20. There is also provided a personal computer (not shown) for an automatic stage control for controlling the turning and parallel movement of the rotary stage 7, the XY stage 14, etc., of the artificial vision system and for outputting images to the monitor 27.

Figure 11:
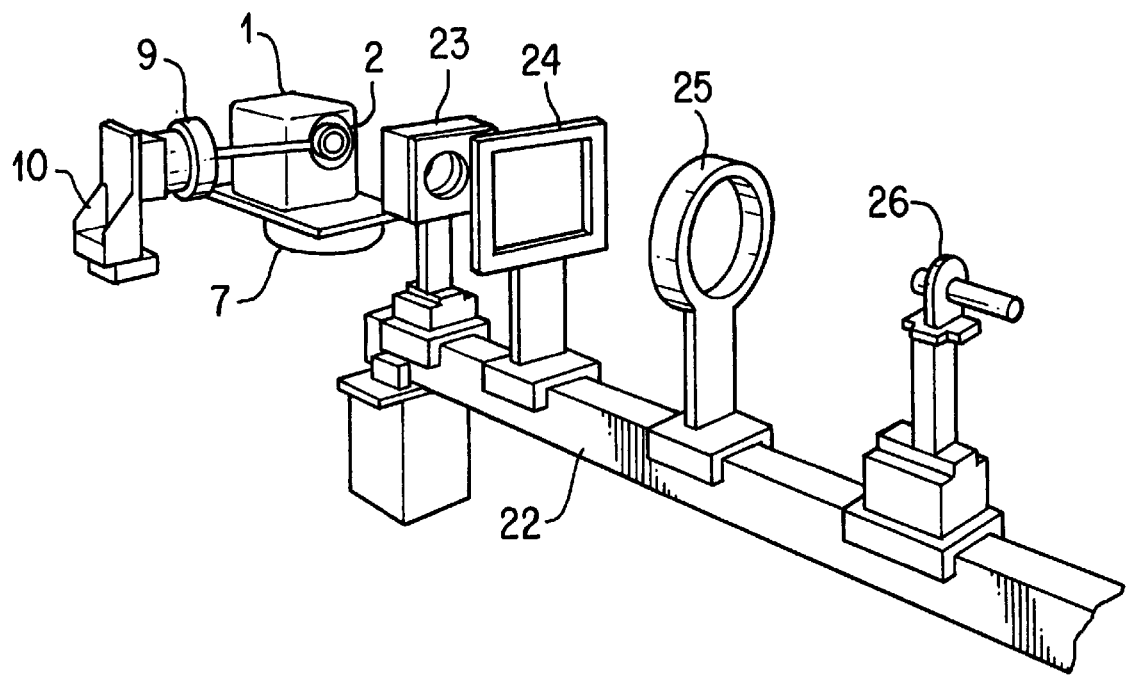
FIG. 11 is a perspective view showing a schematic arrangement for measuring far-sightedness by using the system shown in FIG. 10.

A case of measuring farsightedness by using the system in FIG. 10 will next be explained by reference to FIG. 11. As shown in the figure, the collimator box 23, the diffusing plate 24, the collimator lens 25 and the illuminator 26 are disposed sequentially from the side of the artificial vision camera 1 on the X rail 22. Three dimensional parallel movement and turning are applied to the eyeglass lens 2 and the artificial vision camera 1 by the above-mentioned turning and parallel movement mechanism to make sure that the direction of the optical axis (visual axis) of the artificial vision camera 1 through the eyeglass lens 2 always points to the chart. Light from the illuminator 26 is collimated by the collimator lens 25 and is then irradiated to the diffusing plate 24. The illumination light which has become homogeneous by having been diffused by the diffusing plate 24 is illuminated to the chart on the collimator box 23 and the light (an image) which has been transmitted through the chart is collimated by a collimator lens of the collimator box 23 to be input to the artificial vision camera 1.

Figure 12:
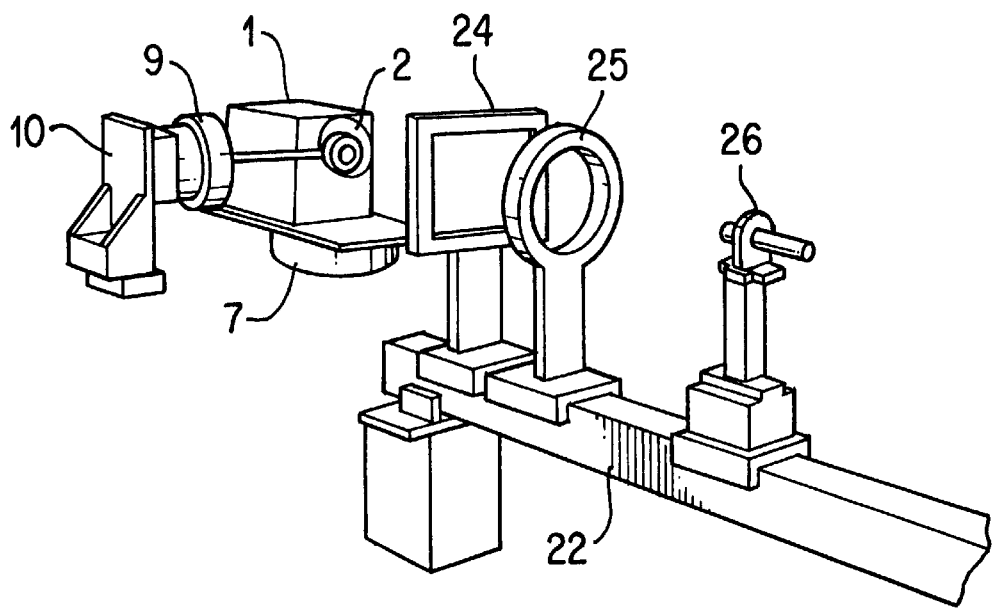
FIG. 12 is a perspective view showing a schematic arrangement in measuring nearsightedness by using the system shown in FIG. 10.
Figure 14A:
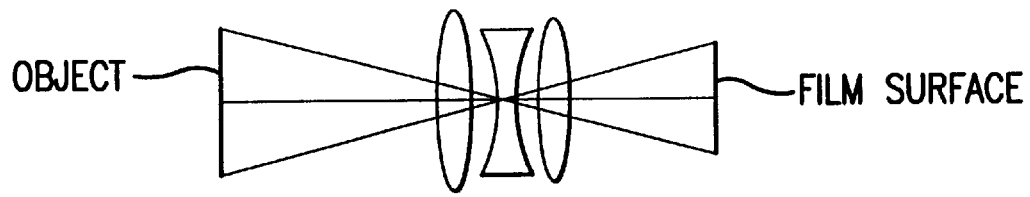
FIGS. 14a and 14b are explanatory diagrams for illustrating differences between an ordinary optical system and an eyeglass optical system.
Figure 14B:
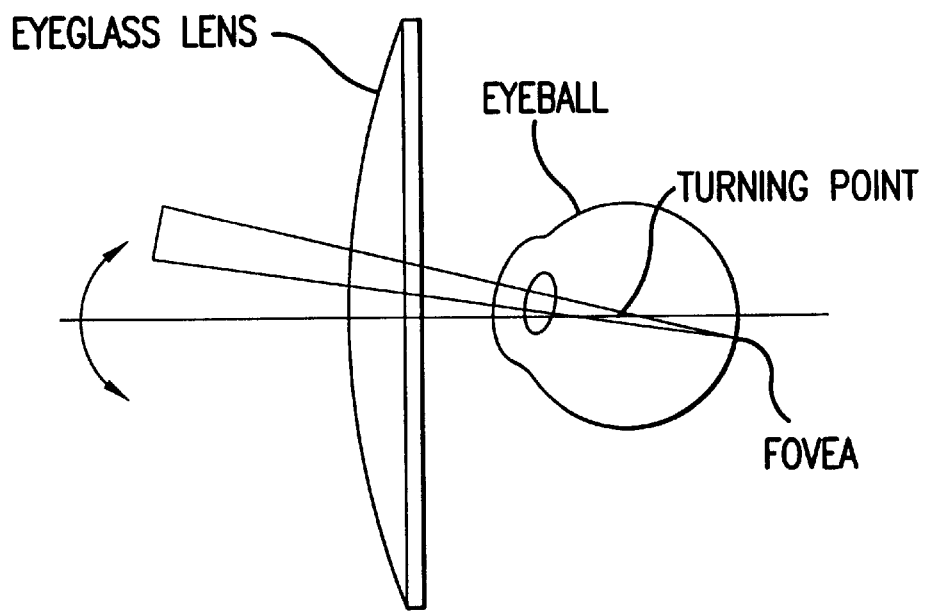

A case of measuring nearsightedness by using the system shown in FIG. 10 will be explained by reference to FIG. 12. The diffusing plate 24, the collimator lens 25 and the illuminator 26 are disposed sequentially from the side of the artificial vision camera 1 on the X rail 22. The chart is attached to the diffusing plate 24. Light from the illuminator 26 is collimated by the collimator lens 25 and is irradiated to the diffusing plate 24. The homogeneous illumination light which has been diffused by the diffusing plate 24 is irradiated to the chart attached to the diffusing plate 24 and the light (an image) which has been transmitted through the chart enters the artificial vision camera 1.

It is also possible to arrange the assembly according to the present invention so as to observe an image through the far-sighted section or the near-sighted section of a eyeglass lens by setting a visual acuity chart in front of the artificial vision camera 1 of the artificial vision system in FIG. 1 without using the system as shown in FIG. 10.

The artificial vision lens system 3 of the present embodiment is adjusted to the optical constants of the paraxial area of the Glustrand's precision simulated eye and is not designed by considering the image forming characteristics. To the contrary, the image in the simulation of images of a currently developed computer visual system is calculated to be a retinal image of the simulated eye which has passed through the eyeglass lens in the respective sight line directions, and is believed to represent the image forming performance on the retina. On the other hand, the image obtained from the artificial vision system of the present invention is an image taken in in a small angle of view (around the fovea of the retina; about 5 degrees) and the image obtained does not represent image forming performance. The evaluation by the observation of the image according to the present system is an utmost relative evaluation.

However, although it is impossible to simulate with a computer when the shape of the eyeglass lens is not known in advance (e.g., an eyeglass lens having a manufacturing error and a eyeglass lens whose design values are unknown) the present artificial vision system allows an image to be observed in real-time by adjusting the standard measuring object (e.g., chart) and the optical axis (visual axis) of the artificial vision camera passing through the eyeglass lens.

Furthermore, while progressive multi-focus lenses and the like are eyeglass lenses for which human technological considerations are taken into account in their optical design, there has heretofore been no lens meter or the like for correctly evaluating such lenses. The present artificial vision system is particularly useful in evaluating such in conjunction with a retinal image simulation obtained by computer.

As described above in detail, according to the present invention, because the artificial vision camera is turned relatively with respect to the eyeglass lens around the turning point of the artificial vision lens system, the positional relationship between the eyeglass lens and the eyeball when the eyeball is turned may be simulated, and the retinal image when one views the standard measuring object through different portions of the eyeglass lens may be obtained by changing the direction of line of sight.

Furthermore, according to the present invention, parallel movement and turning are applied to the eyeglass lens and the artificial vision camera to simulate the positional relationship between the eyeglass lens and the eyeball when the eyeball is turned. Thus, the artificial vision camera heads toward the measuring object at a predetermined position through the eyeglass lens, and a retinal image obtained when a subject views the measuring object through different regions of the eyeglass lens by turning his eyeball may be simulated within a relatively small space and with simple facilities and equipment.

While the present invention has been illustrated by means of certain preferred embodiments, one of ordinary skill in the art will recognize that additions, deletions, substitutions and modifications can be made while remaining within the spirit and scope of the present invention as determined by the appended claims.

What is claimed is:

1. An artificial vision system for simulating a retinal image obtained when an observer views an object through a lens by turning his eyeball, comprising:

an artificial vision camera including an artificial ocular optical system having a simulated turning point and a planar image-pickup;

a lens holder; and a mechanism operably connected to the artificial vision camera to rotate the artificial vision camera around the simulated turning point relative to a lens held in the lens holder.

2. An artificial vision system for simulating a retinal image obtained when an observer views an object through a lens by turning his eyeball, comprising:

an artificial vision camera including an artificial ocular optical system having a simulated turning point and a planar image-pickup;

a lens holder;

a first mechanism operably connected to the artificial vision camera to rotate the artificial vision camera around the simulated turning point relative to a lens held in the lens holder; and a second mechanism operably connected to the holder, to position a lens held in the lens holder relative to the artificial vision camera.

3. An artificial vision system for simulating a retinal image obtained when an observer views an object through a lens by turning his eyeball, comprising:

an artificial vision camera including an artificial ocular optical system having a simulated turning point and a planar image-pickup;

a lens holder;

a first mechanism operably connected to the artificial vision camera to rotate the artificial vision camera around the simulated turning point relative to a lens held in the lens holder;

a second mechanism operably connected to the lens holder to position a lens held in the holder relative to the artificial vision camera; and a standard object;

wherein the first and second mechanisms are operably connected to position said artificial vision camera to point through an eyeglass lens held in the lens holder toward a predetermined location on said standard object.

4. An artificial vision system for simulating a retinal image obtained when an observer views an object through a lens by turning his eyeball, comprising:

an artificial vision camera including an artificial ocular optical system having a simulated turning point and a planar image-pickup;

a lens holder;

a first mechanism operably connected to the artificial vision camera to rotate the artificial vision camera around the simulated turning point relative to a lens held in the lens holder;

a second mechanism operably connected to the lens holder to position a lens held in the holder relative to the artificial vision camera;

a third mechanism operably connected to the first mechanism and second mechanisms to impart rotation and parallel movement to the lens holder and artificial vision camera; and a standard object;

wherein the first and second mechanisms are operably connected to position said artificial vision camera to point through a eyeglass lens held in the lens holder toward a predetermined location on said standard object.

5. An artificial vision system for simulating a retinal image obtained when an observer views an object through a lens by turning his eyeball, comprising:

an artificial vision camera including an artificial ocular optical system having a simulated turning point and a planar image-pickup;

a lens holder;

a first rotation mechanism operably connected to rotate the artificial vision camera about a first vertical z axis passing through the simulated turning point;

a second rotation mechanism operably connected to the lens holder to rotate a lens held in the holder to simulate rotation of the artificial vision camera about a second, horizontal y axis passing through the simulated turning point and normal to the z axis;

a third positioning mechanism operably connected to position the artificial vision camera and the lens holder in an x-y plane normal to the z axis, and to rotate the artificial vision camera and the lens holder about the y axis.

6. A system according to claim 5, wherein the third mechanism further comprises a rotary stage operably connected to rotate both the artificial vision camera and lens holder around the z axis, a gonio stage operably connected to rotate the artificial vision camera and lens holder about the y axis, an xy stage operably connected to move the artificial vision camera and lens holder parallel to x and y axes, and a z stage operably connected to move the artificial vision camera and lens holder parallel to the z axis.

7. A system according to any one of claims 1–6, wherein said artificial vision lens system comprises optical constants of a paraxial area calculated for a simulated eye, the artificial lens system simulating the positional relationship between a lens and an object side principal point of an eyeball.

8. A system according to claim 7, wherein the simulated eye is a Glustrand's precision simulated eye.

9. A system according to claim 5, wherein said artificial vision lens system comprises, sequentially from an object side of said artificial vision camera, a front lens group having negative refracting power, a stop, and a rear lens group having positive refracting power, wherein said system includes a focal point controllable by movement of the rear lens group.

10. A system according to claim 5, wherein said planar image pickup comprises a CCD.

11. A system according to claim 10, further comprising a display connected to display an image picked up by said artificial vision camera.

12. A system according to claim 5, further comprising, sequentially arranged, from a position relatively nearer said artificial vision camera, a first collimator, a diffuser, a second collimator, and an illuminator, and further comprising a rail, operably connected to movably support the sequentially arranged elements.

13. A system according to claim 5, further comprising sequentially arranged from a position relatively nearer said artificial vision camera, a diffuser, a collimator, and an illuminator, and a rail operably connected to movably support the sequentially arranged elements.

14. A method of simulating a retinal image obtained when an observer views an object through a lens by turning his eyeball, comprising the steps of:

providing an artificial vision camera including an artificial ocular optical system having a simulated turning point and a planar image-pickup;

providing a lens holder for holding a lens;

providing a lens;

moving the lens and the artificial vision camera to simulate movement of the artificial vision camera about the turning point.

15. A method according to claim 14, further comprising the steps of providing a standard object, and controlling the movement of the artificial camera and lens so that the camera points to a predetermined position on said object.

16. A method according to claim 15, wherein said step of moving comprises, as necessary to simulate movement of the eye, the further steps of: rotating the artificial vision camera about a first vertical z axis passing through the simulated turning point; rotating a lens held in the holder to simulate rotation of the artificial vision camera about a second horizontal y axis passing through the simulated turning point and normal to the z axis; rotating the artificial vision camera and lens about the y axis, moving the artificial vision camera and lens in an x-y plane normal to the z axis, and moving the artificial vision camera and lens in a direction parallel to the z axis.

* * * * *